May 9, 1972 R. S. MOORE Plant Pat. 3,161
ROSE PLANT
Filed Aug. 24, 1970
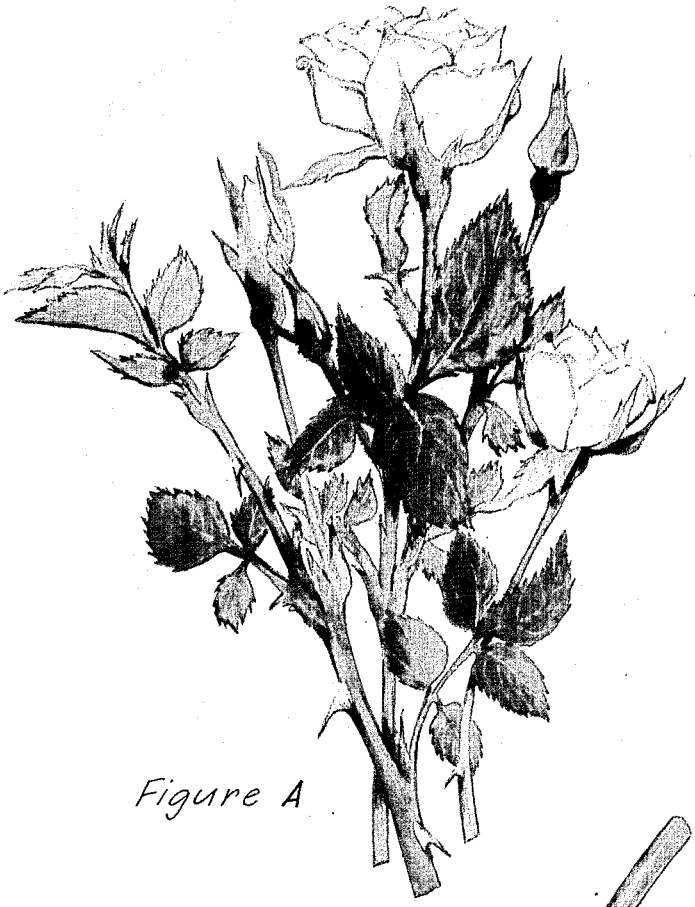
Figure A
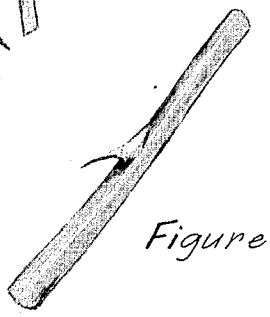
Figure B
WITNESS
Jeanette Nunn Copley
INVENTOR
Ralph S. Moore

United States Patent Office

Plant Pat. 3,161

Patented May 9, 1972

3,161

ROSE PLANT

Ralph S. Moore, 2519 E. Noble Ave., Visalia, Calif. 93277

Filed Aug. 24, 1970, Ser. No. 66,663

Int. Cl. A01h *5/00*

U.S. Cl. Plt.—10 1 Claim

The present invention relates to a new and distinct variety of hardy, dwarf, bush type rose plant of the miniature class; the variety being primarily characterized—as to novelty—by bright orange-red buds and flowers which in general color effect are orange-red.

The variety is further characterized by:

An abundance of bloom, with flowers borne singly or several to stem in loose candelabra clusters.

Little or no fragrance.

A plant which is vigorous, of rounded upright shape, and with semi-glossy, medium small foliage with pointed leaflets; the flowers being similar in size and shape, as compared to the variety Eleanor (United States Plant Patent No. 2,175). The plant which has a normal average height of 12" to 16" at maturity, can easily be maintained at 12" or less with occassional trimming.

A plant which grows and blooms satisfactorily both in greenhouse and outdoors; is a good plant for growing in pots; and provides excellent garden decoration as well as cut flowers.

The present variety of miniature rose was originated by me at my nursery located at Visalia, Calif., under conditions of careful control and observation, as a cross between Baccara (greenhouse hybrid tea, United States Plant Patent No. 1,367) as the seed parent, and Eleanor (Plant Patent No. 2,175) as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; drawf; bush; seedling; greenhouse; outdoors; cut flowers; garden decoration; potted plant.

Class: Miniature.

Flowers:

*Continuity.*—Continuous.

*Fragrance.*—little or none.

Flowers borne: Singly and several together in loose candelabra spray of 4–6 on medium length, quite stiff (wire like) stems.

Quantity of bloom: Average abundance both outside and in greenhouse.

Bud:

*Peduncle.*—Medium to long; slender; erect; light green; smooth.

*Before calyx breaks.*—Size—small.

*Form.*—Pointed; with foliaceous appendages and numerous tiny, very short hairs on surface of the bud; with foliaceous parts extending beyond the tip of the bud equal to one half or more of its length.

*Color.*—Medium green. As calyx breaks; color—red. As first petal opens; red shading into near-white at base.

*Size.*—Small.

*Form.*—Medium length; short-pointed; slightly vase shaped.

*Opening.*—Open well in all weather.

Bloom:

*Size when fully open.*—Small, averaging 1¼" to 1½".

*Petalage.*—Double—25 petals (sometimes a few additional petaloids) arranged regularly.

*Form.*—High centered or slightly cupped at first, with petals rolled loosely outward, and later at maturity remaining loosely rolled outward.

Petals: Rather thick; stiff; satiny both inside and outside. Shape—outside petals broad lanceolate with acute tip; intermediate—lanceolate with acute tip; inside—narrow lanceolate.

Color: Newly opened flower from a plant grown in plastic house (August 1970) Visalia, Calif.

*Outside petal.*—Outside surface—Crimson 22 shading into near-white in lower portion then tipped with light yellow at base; inside surface; Scarlet 19/1 shading into near-white on lower 1/3 of petal, base tipped cream or soft yellow.

*Intermediate petal.*—Outside surface—essentially the same as outside petal—Crimson 22; inside surface—same as outside petal or slightly darker.

*Inside petal.*—Both inside and outside surfaces essentially the same as the intermediate petal.

*General color effect newly opened flower.*—Orange-red.

*Three days open.*—Lighter orange-red or shade of pink similar to Scarlet 19/2.

*Behavior.*—Spent blooms may or may not persist as flower fades, then petals drop.

*Flower longevity (August 1970).*—Bush in garden or pot 4–6 days. Cut flowers at living room temperature—3–4 days (sometimes as much as 7 days).

Reproductive organs:

*Stamens.*—Average; arranged regularly about pistil.

*Filaments.*—Medium length; or varying length, yellow tinted pinkish.

*Pollen.*—Fairly abundant—yellow.

*Pistils.*—Average.

*Styles.*—Short, bunched.

*Stigma.*—Near-white (pinkish).

*Ovaries*—All enclosed in calyx.

*Hips.*—Few or several; globe shaped; orange when ripe.

*Sepals.*—Permanent; spear shaped; straight or incured.

*Seeds.*—Few; low germination.

Foilage:

*Leaves.*—Compound of five leaflets (occasionally 3 or 7); abundant; small (fairly); leathery; semi-glossy to glossy.

*Leaflets.*—Shape—broad lanceolate (almost oval); apex acute; base acute or sometimes rounded. Margin serrate. Color—normal green; new growth sometimes bronze. Rachis—medium strength; upper side grooved; under side sparsely thorny. Stipules—medium to long; medium width; short to medium length points, turning out at an angle of about 45 degrees.

Growth:

*Habit.*—Dwarf, bushy; rounded; much branched.

*Growth.*—Free; vigorous.

*Canes.*—Medium; slender (wirey)

*Main stems.*—Color—dull to waxy green; aging to brown. *Thorns*—moderately thorny; medium length; hooked slightly downward; *color*—medium brown. *Prickles*—none. *Hairs*—none.

*Branches.*—Color—medium to waxy green. *Thorns*—moderately thorney; medium length, slender; hooked slightly downward; medium green color; long oval base. *Prickles*—none. *Hairs*—none.

*New shoots.*—Color—medium green (sometimes tinted bronze). *Thorns*—moderately thorny; medium to long; hooked slightly downward; sharp points; base oval. *Prickles*—none. *Hairs*—none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, rounded, much branched, bush type, as illustrated and described, characterized by buds and flowers resembling the Eleanor rose (miniature—United States Plant Patent No. 2,175) in general shape and size but differing in color, the general color effect of the opening bud and freshly opened flower being a bright shade of orange-red; and further characterized by a plant of compact growth but more vigorous than the Eleanor variety, easy to propagate from cuttings, with medium small semi-glossy foliage, an abundance of bloom borne almost continuously throughout the growing season, with flowers borne singly or in loose candelabra clusters.

No references cited.

ROBERT E. BAGWILL, Primary Examiner